United States Patent [19]

Olin et al.

[11] 4,013,450  
[45] Mar. 22, 1977

[54] HERBICIDAL UREIDO CONTAINING CARBANILATES

[75] Inventors: John F. Olin, Ballwin; Philip C. Hamm, Glendale, both of Mo.

[73] Assignee: Monsanto Company, St. Louis, Mo.

[22] Filed: Feb. 11, 1975

[21] Appl. No.: 549,128

Related U.S. Application Data

[62] Division of Ser. No. 77,677, Oct. 2, 1970, Pat. No. 3,867,426.

[52] U.S. Cl. .................. 71/111; 71/99; 260/293.74; 260/247.1 T; 260/470; 260/471 C; 260/247.2 A; 260/293.77
[51] Int. Cl.² ..................... C07C 127/19
[58] Field of Search ........... 260/240, 247.1, 247.2, 260/552, 553, 293.73, 293.77, 326.4, 468 E, 471 C, 470, 479 C; 71/111, 99

[56] References Cited

UNITED STATES PATENTS

| | | | |
|---|---|---|---|
| 2,993,044 | 7/1961 | Applegath et al. | 260/553 A |
| 3,385,693 | 5/1968 | Luckenbaugh | 260/553 A |
| 3,386,955 | 6/1968 | Nawakowski | 260/553 A |
| 3,434,822 | 3/1969 | Wilson et al. | 260/479 C |
| 3,488,376 | 1/1970 | Ulrich | 260/553 A |
| 3,532,738 | 10/1970 | Wilson et al. | 260/479 C |
| 3,547,979 | 12/1970 | Brantley | 260/479 C |
| 3,567,764 | 3/1971 | Brantley | 260/479 C |
| 3,622,617 | 11/1971 | Windel et al. | 260/468 E |
| 3,642,891 | 2/1972 | Teach | 260/553 A |
| 3,646,136 | 2/1972 | Hoegerle et al. | 260/553 A |
| 3,661,989 | 5/1972 | Nawakowski | 260/553 A |
| 3,670,010 | 6/1972 | Teach | 260/479 C |
| 3,701,807 | 10/1972 | Chupp | 260/553 A |
| 3,707,556 | 12/1972 | Teach | 260/553 A |
| 3,734,961 | 5/1973 | Englehart | 260/553 A |
| 3,801,625 | 4/1974 | Young et al. | 260/479 C |
| 3,806,536 | 4/1974 | Dorschner et al. | 260/479 C |
| 3,806,537 | 4/1974 | Dorschner et al. | 260/479 C |
| 3,879,441 | 4/1975 | Boroschewski et al. | 260/471 |

OTHER PUBLICATIONS

Vasilev et al., Chem. Abst., vol. 74, item 30948 (1971) (article published in 1969).
Bruce, et al. Proc. Roy. Soc. (London) Ser. B, vol. 165, pp. 245-253 (1966).
Chemical Abstracts Subject Index, vol. 68, p. 39215 (1966).
Chemical Abstracts Cumulative Subject for 1967–1971, p. 324635.

*Primary Examiner*—John D. Randolph
*Assistant Examiner*—R. W. Ramsuer
*Attorney, Agent, or Firm*—Richard H. Shear

[57] ABSTRACT

Novel compounds and their herbicidal use having the formula

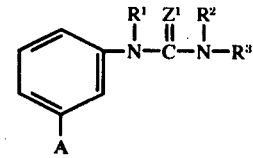

wherein A is selected from the group

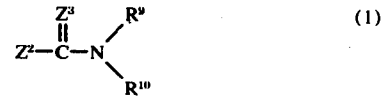 (1)

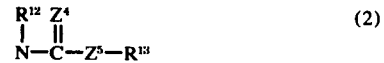

(2)

or 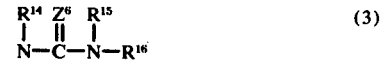 (3)

6 Claims, No Drawings

HERBICIDAL UREIDO CONTAINING CARBANILATES

This is a division of application Ser. No. 77,677 filed Oct. 2, 1970 now U.S. Pat. No. 3,867,426.

This invention relates to novel meta-bifunctional substituted benzenes. This invention further relates to herbicidal compositions and methods of herbicidal use utilizing the novel meta-bifunctional substituted benzenes of this invention.

The novel meta-bifunctional substituted benzenes of this invention are of the formula.

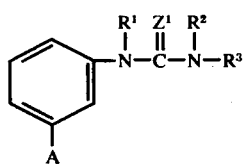

wherein $Z^1$ is selected from the group consisting of oxygen and sulfur; $R^1$ is selected from the group consisting of hydrogen, alkyl having a maximum of 8 carbon atoms and alkenyl having a maximum of 6 carbon atoms; $R^2$ is selected from the group consisting of hydrocarbyl selected from the group consisting of alkyl, alkenyl, alkynyl and cycloalkyl said alkyl, alkenyl and alkynyl having a maximum of 12 carbon atoms and said cycloalkyl having 3 to 7 ring carbon atoms and a maximum of 4 chain carbon atoms, alkoxy having a maximum of 6 carbon atoms, chloroalkyl having a maximum of 6 carbon atoms and a maximum of 3 halogen atoms, chloroalkenyl having a maximum of 6 carbon atoms and a maximum of 3 halogen atoms, cycloalkenyl having 5 to 7 ring carbon atoms and a maximum of 4 chain carbon atoms, phenyl, substituted phenyl having a maximum of two substituents said substituents being selected from the group consisting of halogen, nitro and alkyl having a maximum of 4 carbon atoms, the group

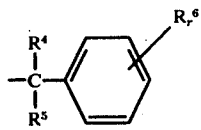

wherein $R^4$ and $R^5$ are each independently selected from the group consisting of hydrogen, alkyl having a maximum of 12 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms; $R^6$ is selected from the group consisting of halogen, alkyl having a maximum of 14 carbon atoms, chloroalkyl having a maximum of 3 carbon atoms and a maximum of 3 halogen atoms, nitro, and alkoxy having a maximum of 3 carbon atoms; and r is one of the integers zero to three; the group

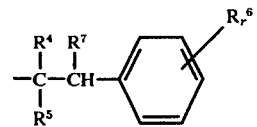

wherein $R^7$ is selected from the group consisting of alkyl and alkenyl each having a maximum of 4 carbon atoms, and $R^4$, $R^5$, $R^6$ and r are as previously defined; and $R^3$ is selected from the group consisting of hydrogen, alkyl having a maximum of 12 carbon atoms, and alkenyl having a maximum of 8 carbon atoms, $R^2$ and $R^3$ can with the nitrogen form the group selected from the group consisting of

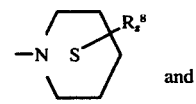

and

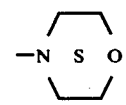

provided that when $R^2$ or $R^3$ is unsaturated the position of unsaturation is other than on the 1-carbon atom; wherein $R^8$ is alkyl having a maximum of 3 carbon atoms and s is one of the integers zero to two;

A is selected from the group consisting of

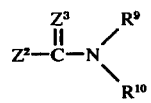

wherein $Z^2$ and $Z^3$ are independently selected from the group consisting of oxygen or sulfur; $R^9$ is selected from the group consisting of hydrocarbyl selected from the group consisting of alkyl, alkenyl, alkynyl and cycloalkyl said alkyl, alkenyl and alkynyl having a maximum of 12 carbon atoms and said cycloalkyl having 3 to 7 ring carbon atoms and a maximum of 4 chain carbon atoms, chloroalkyl having a maximum of 15 carbon atoms and a maximum of 3 halogen atoms, chloroalkenyl having a maximum of 12 carbon atoms and a maximum of 3 halogen atoms and alkoxyalkyl having a maximum of a total of 12 carbon atoms, the group $-CH_2(CH_2)_xOR^{17}$ wherein x is one of the integers zero to four and $R^{17}$ is selected from the group consisting of phenyl, naphthyl, substituted phenyl and substituted naphthyl said substitution being a maximum of 3 substituents and said substituent being independently selected from halogen and alkyl having a maximum of 4 carbon atoms, $-CH_2CH=CH$-phenyl, the group

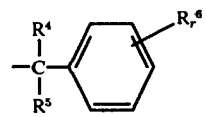

-continued

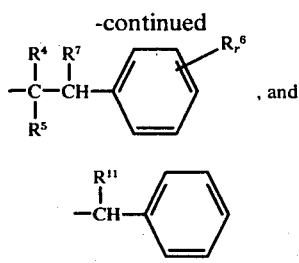
, and wherein $R^{11}$ is selected from the group consisting of phenyl and naphthyl and $R^4$, $R^5$, $R^6$, $R^7$ and $r$ are as previously defined; $R^{10}$ is selected from the group consisting of hydrogen, alkyl having a maximum of 12 carbon atoms, cycloalkyl having 5 to 7 carbon atoms, alkenyl having a maximum of 4 carbon atoms, chloroalkyl having a maximum of 6 carbon atoms and a maximum of 3 halogen atoms and chloroalkenyl having a maximum of 4 carbon atoms and a maximum of 3 halogen atoms; provided that when $R^2$ is a hydrocarbyl group having less than 9 carbon atoms then $R^9$, when a hydrocarbyl group, has at least 8 carbon atoms;

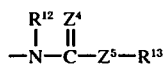 II wherein $Z^5$ and $Z^6$ are each independently selected from the group consisting of oxygen and sulfur; $R^{12}$ is selected from the group consisting of hydrogen, alkyl having a maximum of 6 carbon atoms and alkenyl having a maximum of 6 carbon atoms; and $R^{13}$ is selected from the group consisting of alkyl having a maximum of 8 carbon atoms, alkenyl having a maximum of 6 carbon atoms, cycloalkyl having from 3 to 7 ring carbon atoms, cyclohexenyl, phenyl, substituted phenyl having a maximum of two substituents said substituents being selected from the group consisting of halogen, nitro and alkyl having a maximum of 4 carbon atoms, the group

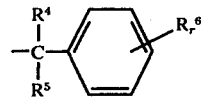

and the group

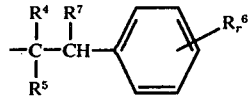

wherein $R^4$, $R^5$, $R^6$, $R^7$ and $r$ are as previously defined; and

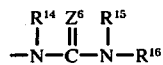 III wherein $Z^6$ is selected from the group consisting of oxygen and sulfur;
$R^{14}$ is selected from the group consisting of hydrogen, alkyl having a maximum of 8 carbon atoms and alkenyl having a maximum of 6 carbon atoms; $R^{15}$ is selected from the group consisting of alkyl having a maximum of 12 carbon atoms, alkenyl having a maximum of 7 carbon atoms, alkoxy having a maximum of 6 carbon atoms, chloroalkyl having a maximum of 6 carbon atoms, and a maximum of 3 halogen atoms, chloroalkenyl having a maximum of 6 carbon atoms and a maximum of 3 halogen atoms, cycloalkyl having 3 to 7 ring carbon atoms and a maximum of 4 chain carbon atoms, cycloalkenyl having 5 to 7 ring carbon atoms and a maximum of 4 chain carbon atoms, phenyl, substituted phenyl having a maximum of two substituents said substituents being selected from the group consisting of halogen, nitro and alkyl having a maximum of 4 carbon atoms, the group

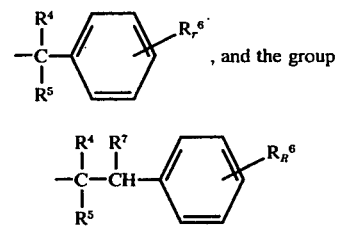, and the group wherein $R^4$, $R^5$, $R^6$, $R^7$ and $r$ are as previously defined; and $R^{16}$ is selected from the group consisting of hydrogen, alkyl having a maximum of 12 carbon atoms and alkenyl having a maximum of 8 carbon atoms; $R^{15}$ and $R^{16}$ can with the nitrogen form the group selected from the group consisting of

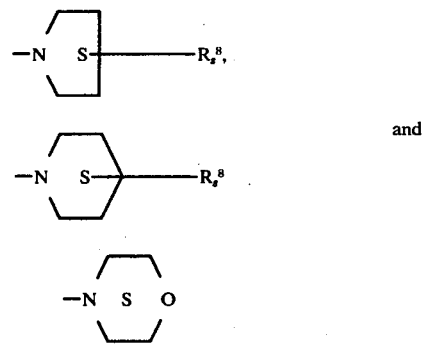

and wherein $R^8$ and $s$ are as previously defined.

A preferred embodiment of this invention are the compounds wherein only one of $R^4$ and $R^5$ is alkenyl or chloroalkenyl and that $R^7$ is other than alkenyl when either $R^4$ or $R^5$ is alkenyl or chloroalkenyl.

Another preferred embodiment of this invention is the class of compounds of the formula

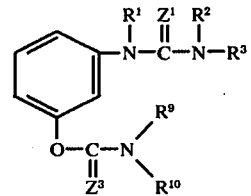

wherein $R^1$, $R^2$, $R^3$, $R^9$, $R^{10}$, $Z^1$ and $Z^3$ are as previously defined in the above preferred embodiment.

Within this class of compounds preferred embodiments are those compounds in which $R^1$ is hydrogen or alkyl having a maximum of 4 carbon atoms.

A further embodiment, within this class, are those compounds in which $R^1$ is hydrogen and $R^2$ is selected from the group consisting of chloroalkyl having a maximum of 6 carbon atoms and a maximum of 3 halogen atoms, chloroalkenyl having a maximum of 6 carbon atoms and a maximum of 3 halogen atoms, the group

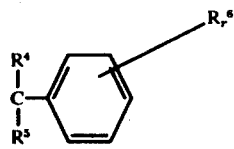

and the group

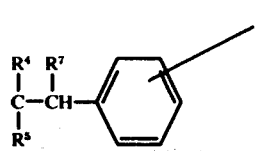

wherein $R^3$, $R^4$, $R^5$, $R^6$, $R^7$, $R^9$, $R^{10}$, $Z^3$ and r are as previously defined.

A still further embodiment, within this class, are those compounds in which $R^1$ is hydrogen, $R^9$ is selected from the group consisting of chloroalkyl having a maximum of 12 carbon atoms and a maximum of 3 halogen atoms, chloroalkenyl having a maximum of 8 carbon atoms and a maximum of 3 halogen atoms, —$CH_2CH$=$CH$-phenyl and the group

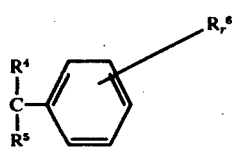

and

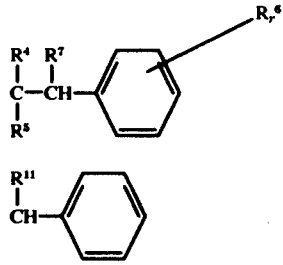

wherein $R^2$, $R^3$, $Z^1$, $Z^3$, $Z^4$, $R^5$, $R^6$, $R^7$, $R^{11}$ and r are as previously defined; and $R^{10}$ is selected from the group consisting of hydrogen, alkyl having a maximum of 12 carbon atoms, cycloalkyl having 5 to 7 ring carbon atoms, alkenyl having a maximum of 4 carbon atoms, chloroalkyl having a maximum of 6 carbon atoms and a maximum of 3 halogen atoms and chloroalkenyl having a maximum of 4 carbon atoms and a maximum of 3 halogen atoms.

Another preferred embodiment of this invention are the compounds of the formula

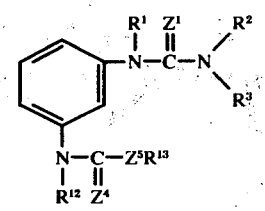

wherein $R^1$ is selected from the group consisting of hydrogen and alkyl having a maximum of 4 carbon atoms; and $R^{12}$ is selected from the group consisting of hydrogen and alkyl having a maximum of 4 carbon atoms; and $R^2$, $R^3$, $Z^1$, $Z^4$ and $R^5$ are as previously defined in the preferred embodiment.

Another embodiment, within this class, are those compounds in which $R^1$ and $R^{12}$ are both hydrogen.

A still further embodiment of this invention are those compounds of the formula

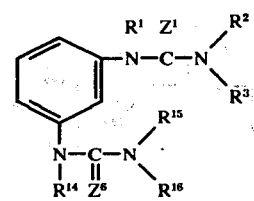

wherein $R^1$ and $R^{14}$ are each independently selected from the group consisting of hydrogen and alkyl having a maximum of 4 carbon atoms; and $R^2$, $R^3$, $R^{15}$, $R^{16}$, $Z^1$ and $Z^6$ are as previously defined in the preferred embodiment.

The meta bifunctional compounds of this invention can be prepared by a process represented by the following equation:

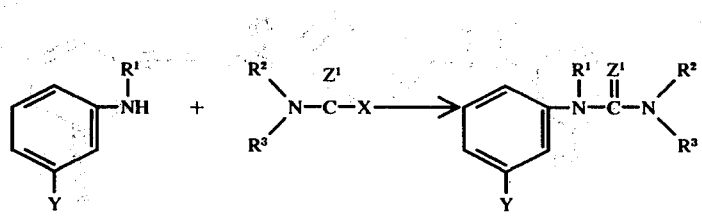

wherein Y is SH, OH or $NO_2$; X is chloro or bromo; and $R^1$, $R^2$ and $R^3$ are as previously defined.

When Y is hydroxy or mercapto the following synthesis represents a mode of preparations of the desired compounds:

II 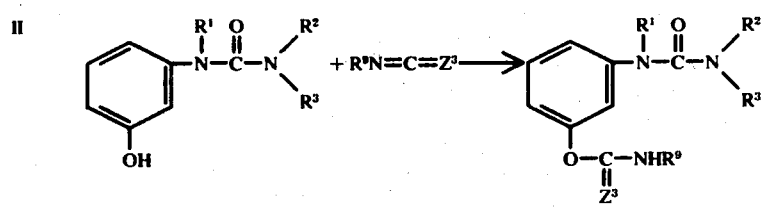

Or

III 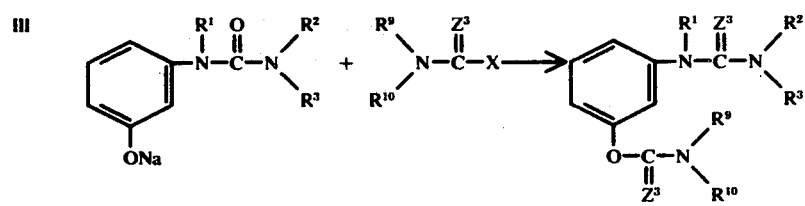

wherein $R^1$, $R^2$, $R^3$, $R^9$, $R^{10}$, $Z^3$ and X are as previously defined.

When Y is nitro the following synthesis represents a mode of preparation of the desired compounds:

(4) 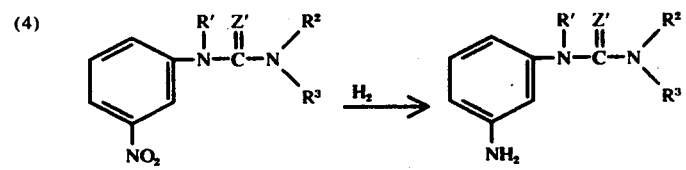

(5) 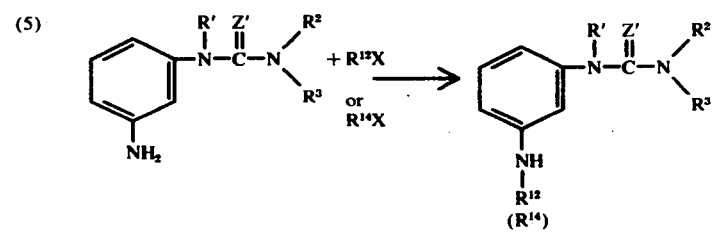

(6) 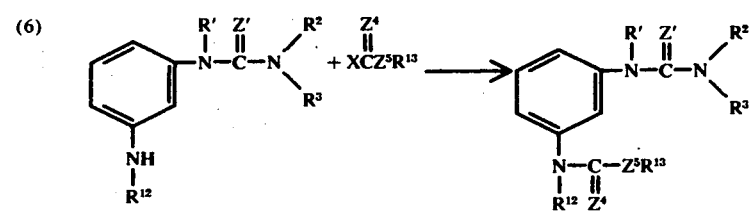

or (7) 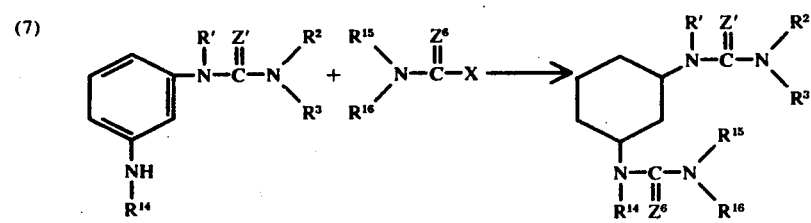

wherein $R^1$, $R^2$, $R^3$, $R^{12}$, $R^{13}$, $R^{14}$, $R^{15}$, $R^{16}$, $Z^1$, $Z^4$, $Z^5$, $Z^6$ and X are as previously defined.

The above reactions are represented equations as to modes of preparation of the desired compounds. Other modes are available and are listed in the literature and the following examples.

The starting nitroanilines or hydroxyanilines are commercially available or are easily prepared by known methods.

Hydrogenation of the nitro group may be by any of the procedures known to those skilled in the art, such as catalytic hydrogenation; metal-acid combinations such as iron-acid; metal-alcohol combinations such as zinc dust or aluminum amalgams and aqueous alcohol; lithium aluminum hydride and the like.

The procedure used may depend upon the groups already present on the ring. These procedures are also well known to those skilled in the art. A preferred procedure is catalytic hydrogenation utilizing 5% palladium on charcoal.

In the above reaction sequences it is not required that the urea group be formed first. The second group may be formed first followed by hydrogenation of a nitro group and formation of the urea group. The actual method used depends upon convenience and nature of group to be formed. This will be illustrated in the examples showing the preparation of some of the starting compounds from which the urea function is then formed as illustrated in the equations.

The above reaction equation shows the interrelationship of the three groups of compounds. The reactions, starting compounds, intermediates and/or reactants to form each group are common to the groups.

It will be shown hereinafter that this interrelationship of the groups also extends to their herbicidal activity.

The following examples will illustrate the invention. In the following examples as well as in the specification and appended claims, parts and percent are by weight unless otherwise indicated.

EXAMPLE 1

This example describes the preparation of 3-(3'-hydroxyphenyl)-1,1-dimethylurea.

To a suitable vessel charged with 343.5 parts m-aminophenol in 1800 parts ethyl acetate was added 187 parts dimethylcarbamoyl chloride and the resultant mixture stirred at room temperature for 15 hours. To this mixture was then added 177 parts triethylamine and the mixture stirred for 6 hours. Dimethylcarbamoyl chloride (187 parts) was then added and the resultant mixture stirred 72 hours at room temperature. The solid which separated was filtered and washed with ethyl acetate and then water and then air dried. mp 199.5°–201° C.

EXAMPLE 2

This example describes the preparation of 1,1-dimethyl-3-[3'-(N-alpha-methylbenzylcarbamoyloxy)-phenyl] urea.

To a suitable vessel charged with 44.4 parts tetrahydrofuran, 23.6 parts dimethylformamide and 1.45 parts triethylamine was added, with stirring, 18 parts 1,1-dimethyl-3-(3'-hydroxyphenyl)urea. To the resultant mixture was added, with stirring, 16.2 parts alpha-methylbenzyl isocyanate. The solution was stirred at about 35° C for 2 hours and then left standing at room temperature for about 15 hours. A solution of ethyl ether-hexane (128.5 parts ethyl ether and 79.1 parts n-hexane) was added to the mixture, with stirring, and then filtered and the crystals washed with ethyl ether and dried. mp 167–168° C Analysis for $C_{18}H_{21}N_3O_3$: Calc'd: C, 66.06; H, 6.47; N, 12.84. Found: C, 66.24; H, 6.36; N, 12.67.

EXAMPLE 3

This example describes the preparation of 1,1-dimethyl-3-[3'-(n-alpha t-butyl-4-methoxybenzylcarbamoyloxy)phenyl] urea.

This example follows the procedure of Example 2 substituting 24.01 parts of alpha t-butyl-4-methoxybenzyl isocyanate for the alpha methylbenzyl isocyanate. The product, recrystallized from methanol-water, melted 215°–217° C.

Analysis for $C_{22}H_{29}N_3O_4$: Calc'd C, 66.14; H, 7.32; N, 10.52. Found: C, 66.21; H, 7.32; N, 10.63.

EXAMPLE 4

This example describes the preparation of 1-(2-chloroallyl)-1-dodecyl-3-[3'-(N-methylcarbamoyloxy)phenyl] urea.

To a suitable vessel charged with 245 parts m-hydroxy-phenylisothiocyanate and 450 parts ethyl acetate was added, with stirring, 3.6 parts triethylamine and then, over about a one half hour period, 114 parts methyl isocyanate. The reaction temperature increased to about 60° C. The resultant mixture was stirred for about 30 minutes, cooled and 330 parts n-hexane added during which time crystals separated from solution. To the mixture was then added 390 parts of a solution, containing 225 parts ethyl acetate and 165 parts n-hexane, and the mixture cooled to 5° C. The mixture was filtered and the crystals, m-(N-methylcarbamoyloxy)phenyl-isocyanate washed with an ethyl acetate-n-hexane (2:3 volivol) solution. mp 98°–99° C To a suitable vessel charged with 4.2 parts m-(N-methylcarbamoyloxy)phenylisocyanate was added 5.3 parts N-(2-chloroallyl)dodecylamine in 16 parts methanol. The resultant mixture was heated to about 60° C and then water added until the mixture turned cloudy. The resultant mixture was then allowed to stand, overnight, at room temperature. The ether was then removed yielding the product, mp 112°–113° C.

Analysis for $C_{24}H_{38}ClN_3O_2S$: Calc'd: N, 8.98; S, 6.85; Found: N, 9.18; S, 6.95.

EXAMPLE 5

This example describes the preparation of 1,1-dimethyl-3-[3'-(3''-(2-phenoxyethyl)ureido)phenyl] urea of the formula

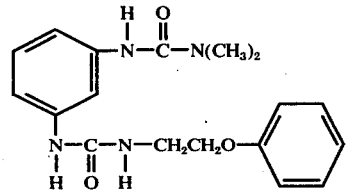

To a suitable vessel charged with 17.92 parts 1,1-dimethyl-3-(m-aminophenyl)urea, 23.6 parts dimethylformamide, 44.4 parts tetrahydrofuran and 0.363 parts triethylamine was added, with stirring, 16.32 parts 2-phenoxyethylisocyanate (prepared from 2-phenoxyethylamine and phosgene), and the resultant mixture stirred for about 2 hours. Ethyl ether, 286 parts, was then added during which time a precipitate started to form. The mixture was allowed to stand overnight, then filtered and the solid washed with ethyl ether and air dried. mp 133–136° C Analysis for $C_{18}H_{22}N_4O_3$: Calc'd; C, 63.14; H, 6.48; N, 16.36. Found: C, 63.31; H, 6.70; N, 16.31.

EXAMPLE 6

This example describes the preparation of 1,1-dimethyl-3-[3'-(3''-(alpha, 4-dimethyl-benzyl)ureido)-phenyl] urea of the formula

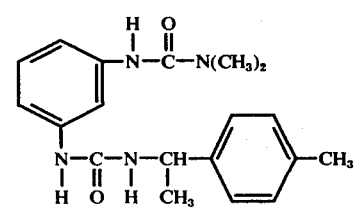

This example is similar to Example 5, substituting 16.12 parts alpha, 4-dimethylbenzylisocyanate for the 2-phenoxyethylisocyanate, yielding the product melting 203°–205° C.

Analysis for $C_{19}H_{24}N_4O_2$: Calc'd C, 67.03; H, 7.11; N, 16.46. Found: C, 67.25; H, 7.19; N, 16.49.

EXAMPLE 7

This example describes the preparation of 3-[3'-(N, alpha,4-dimethylbenzyl-N-methylcarbamoyloxy)-phenyl]-1,1-dimethylurea.

To a suitable vessel charged with 60 parts sodium methoxide and 633 parts methanol was added, with stirring, a solution consisting of 180 parts 1,1-dimethyl-3-(m-hydroxyphenyl) urea and 802 parts methanol. The resultant mixture was stirred and the methanol removed under reduced pressure until a dry solid was obtained. The solid, sodium salt of 1,1-dimethyl-3-(m-hydroxyphenyl) urea, was washed with benzene.

To a suitable vessel charged with 17.4 parts sodium salt of 1,1-dimethyl-3-(m-hydroxyphenyl) urea (prepared above) and 57.95 parts acetonitrile was added with stirring 12.7 parts N-methyl-N-alpha, 4-di-methylbenzylcarbamoyl chloride and the mixture stirred about 2 hours at room temperature and then let stand for about 2 days at room temperature. The solvent was then removed under reduced pressure and the residue dissolved in toluene. The toluene solution was extracted with water, dried and concentrated. The resultant oil was taken up in xylene from which the product, as a solid was obtained, mp 113°–116° C.

Analysis for $C_{20}H_{25}N_3O_3$: Calc'd C, 67.58; H, 7.09; N, 11.82. Found: C, 67.74; H, 7.16; N, 11.72.

EXAMPLE 8

This example describes the preparation of methyl m-aminocarbanilate.

To a suitable vessel charged with 500 parts m-nitroaniline, 315 parts potassium carbamate, 800 parts water, 800 parts ice and 901 parts ethyl acetate was added, with stirring, 380 parts methyl chloroformate over about a 2 hour period, white maintaining the reaction temperature at below about 15° C. Hexane (330 parts) was then added and the resultant mixture stirred about 2 hours at 25 to 30° C. The mixture was then filtered and the solid washed with a 1:1 mixture of n-hexane-ethyl acetate, then with water and dried. The productmethyl m-nitrocarbanilate-melted at 148°–150° C.

To a suitable hydrogenation apparatus was charged 664 parts methyl m-nitrocarbanilate, 9 parts palladium on carbon and 1241 parts dioxane. The apparatus was then purged and pressurized to 800 psi with hydrogen. On agitation, the temperature rose slowly to about 80° C and then dropped and the pressure dropped to 0 psi. The temperature was about 50° C when the pressure was 0 psi. The apparatus was repressurized to 500 psi and the temperature rose to 85° C. Process was repeated until no pressure drop or temperature rise was noted. The mixture was agitated in the system for an additional hour, and then the apparatus vented and the mixture filtered. The solvent was removed under reduced pressure until a pot temperature of 80° C/ 0.2 mm pressure was obtained. The oil which was obtained crystallized on standing-mp 67°–69° C. Recrystllization from methanol and then ethyl acetate-tolunene-methylcyclohexane yielded the product melting 71°–71.5° C.

EXAMPLE 9

This example describes the preparation of methyl m-(3-t-butylureido)carbanilate of the formula

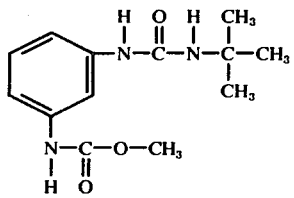

A suitable vessel was charged with 16.6 parts methyl m-aminocarbanilate, prepared in Example 8, 88.8 parts tetrahydrofuran, 14.9 parts t-butylisocyanate and 0.73 parts triethylamine and the resultant mixture refluxed for about 8 hours. To the hot mixture was added 132 parts n-hexane and the mixture allowed to cool overnight. The solvent was removed under reduced pressure and the solid residue stirred with 300 parts of a 4% hydrochloric acid solution. The mixture was filtered and the solid washed with water. The solid product was recrystallized from methanol. mp 145°–147° C

EXAMPLE 10

This example describes the preparation of methyl m-[3-(1,1,3,3-tetramethylbutyl)ureido]carbanilate of the formula

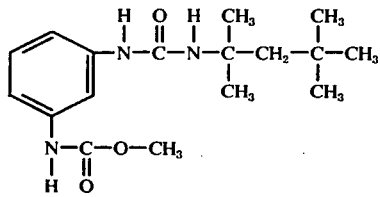

The process of Example 9 was followed substituting 21 parts 1,1,3,3-tetramethylbutylisocyanate for 14.9 parts t-butylisocyanate. The product melted at 152°–153° C.

The following carbamoyloxyureas were prepared by substantially the same procedure as previously shown. In the naming of the compounds a C = S in the urea group is referred to as thiourea. Replacement of sulfur for oxygen in the carbamoyloxy group will be named as follows:

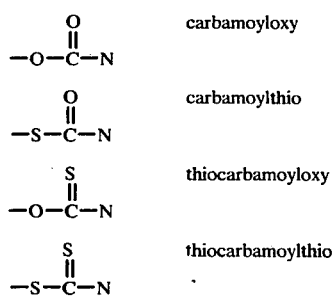

The nitrogen of the urea group attached to the meta-bifunctional phenyl will be the 3-position nitrogen. The nitrogen of the carbamoyloxy group will be indicated as "N'".

3-[3'-(N'-3,4-dichlorophenylcarbamoyloxy)phenyl]-1-(3,4-dichlorophenyl)urea

3-[3'-methylcarbamoyloxy)phenyl]-1-(2-chloroalkyl)-2-thiourea

3-[3'-(N'-alpha-methylbenzylcarbamoyloxy)-phenyl]-1,1-dimethylurea

3-[3'-(N'-alpha-methylbenzylcarbamoyloxy)-phenyl]-1-tert-butyl-2-thiourea

3-[3'-(N'-methylcarbamoyloxy)phenyl]-1-(2-chlorobenzyl)-2-thiourea

3-[3'-(N'-methylcarbamoyloxy)phenyl]-1-(4-chlorobenzyl)-2-thiourea

3-[3'-(N'-methylcarbamoyloxy)phenyl]-1-(1-naphthyl)-2-thiourea

3-[3'-(N'-methylcarbamoyloxy)phenyl]-1,1-di-n-octyl-2-thiourea

3-[3'-(N'-methylcarbamoyloxy)phenyl]-1-(2-chloroallyl)-1-dodecyl-2-thiourea

3-[3'-(N'-methylcarbamoyloxy)phenyl]-1-phenyl-1-(alpha-methylbenzyl)-2-thiourea

3-[3'-(N'-methylcarbamoyloxy)phenyl]-1-(1,1,3,3-tetramethylbutyl)-2-thiourea

3-[3'-(N'-methylcarbamoyloxy)phenyl]-1-methyl-1-(2-chloroallyl)-2-thiourea

3-[3'-(N'-methylcarbamoyloxy)phenyl]-1,1-dipropargyl-2-thiourea

3-[3'-(N'-methylcarbamoyloxy)phenyl]-1-propargyl-1-benzyl-2-thiourea

3-[3'-(N'-methylcarbamoyloxy)phenyl]-1-methyl-1-octadecyl-2-thiourea

3[3'-(N',N'dimethylcarbamoyloxy)phenyl]-1-methyl-1-(2-chloroallyl)-2-thiourea

3-[3'-(N',N'-diethylcarbamoyloxy)phenyl]-1-methyl-1-(2-chloroallyl)-2-thiourea

3-[3'-(N'-methyl-N'-n-butylcarbamoyloxy)phenyl]-1-methyl-1-(2-chloroallyl)-2-thiourea 3-[3'-(N'-1-pyrolidylcarbamoyloxy)phenyl]-1-methyl-1-(2-chloroallyl)-2-thiourea 3-(3'-(N,N'-di-n-butylcarbamoyloxy)phenyl]-1-methyl-1-(2-chloroallyl)-2-thiourea 3-[3'-(N'-methyl-N'-benzylcarbamoylocy)phenyl]-1-methyl-1-(2-chloroallyl)-2-thiourea 3-[3'-(N'-t-butylcarbamoyloxy)phenyl]-1-methyl-1-(2-chloroallyl)-2-thiourea 3-[3'-(N'-n-butylcarbamoyloxy)phenyl]-1-methyl-1-(2-chloroallyl)-2-thiourea 3-[3'-(N'-allylcarbamoyloxy)phenyl]-1-methyl-1-(2-chloroallyl)-2-thiourea 3-[3'-(N'-cyclohexylcarbamoyloxy)phenyl]-1-methyl-1-(2-chloroallyl)-2-thiourea 3-[3'-(N'-alpha-methylbenzylcarbamoyloxy]-1-methyl-1-(2-chloroallyl)-2-thiourea 3-[3'-phenylcarbamoyloxy)phenyl]-1-methyl-1-(2-chloroallyl)-2-thiourea 3-[3'-(N'-3-chlorophenyl)phenyl]-1-methyl-1-(2-chloroallyl)-2-thiourea 3-[3'-N'-methylcarbamoyloxy)phenyl]-1-methyl-1-cyclododecyl-2-thiourea 3-[3'-(N'-methylcarbamoyloxy)phenyl]-1-methyl-1-2-phenylethyl)-2-thiourea 3'[3'-(N'-methylcarbamoyloxy)phenyl]-1-(1,1-dimethyl-2-phenylethyl)-2-thiourea 3-[3'-(N'-methylcarbamoyloxy)phenyl]-1-methyl-1-naphthyl-2-thiourea 3-[3'-(N'-methylcarbamoyloxy(phenyl]-1-methyl-1-(1-naphthylmethyl)-2-thiourea 3-[3-(N'-methylcarbamoyloxy)phenyl]-1-(alphaisopropylbenzyl)-2-thiourea 3-[3'-(N'-methylcarbamoyloxy)phenyl]-1-(alpha-t-butyl-4-methoxybenzyl)-2-thiourea 3-[3'-(N'-1-pyrrolidylcarbamoyloxy)phenyl]-1-methyl-1-(1-naphthylmethyl)-2-thiourea 3-[3'-(N',N'-dimethylcarbamoyloxy)phenyl]-1-methyl-1-(1-naphthylmethyl)-2-thiourea 3-[3'-(N'-methyl-N'-2-chlorobenzylcarbamoyloxy)-phenyl]-1,1-dimethylurea 3'[3'-(N'-ethyl-N'-4-chlorobenzylcarbamoyloxy)-phenyl]-1,1-dimethylurea 3-[3'-(N'-t-butylcarbamoyloxy)phenyl)]-1-isopropyl-1-(2-phenethyl)urea 3-[3'(N'-allyl-N'-2-phenylethylcarbamoyloxy)-phenyl]-1,1-dimethylurea 3-[3'-(N'-4-chlorobenzylcarbamoyloxyphenyl]-1,1-dimethylurea 3-3-N'-alpha methyl-4-chlorobenzylcarbamoyloxy)-phenyl]-1,1-dimethylurea 3-[3'-(N'-alpha ethylbenzylcarbamoyloxyphenyl]-1,1-dimethylurea 3-[3'-(N'-alpha isopropylbenzylcarbamoyloxy)-phenyl]-1,1-dimethylurea 3-[3'-(N'-4-methylbenzylcarbamoyloxy)phenyl]-1,1-dimethylurea 3-[3'-(N'-t-butylcarbamoyloxy)phenyl]-1-methyl-1-benzylurea 3-[3'-(N'-benzylcarbamoyloxy)phenyl)-1-methyl-1-benzylurea 3-[3'-(N'-cyclohexylcarbamoyloxy)phenyl]-1-methyl-1-benzylurea 3-[3'-(N'-phenylcarbamoyloxy)phenyl]-1-methyl-1-benzylurea 3-[3'-(N'-methylcarbamoyloxy)phenyl]-1-methyl-1-benzylurea 3-[3'-(N'-methyl-N'-benzylcarbamoyloxy)phenyl]-1-methyl-2-thiourea 3-[3'-(N'-methylcarbamoyloxy)phenyl]-1-allyl-2-thiourea 3-[3'-(N'-methyl-N'-2-(2-methyl-4-chlorophenoxy)ethylcarbamoyloxy)phenyl]-1,1-dimethylurea 3-[3'-(N'-alpha,4-dimethylbenzycarbamoyloxy)-phenyl]-1,1-dimethylurea 3-[3'-(N'-1,1-dimethyl-2-phenethylcarbamoyloxy)phenyl]-1,1-dimethylurea 3-[3'-(N'-methyl-N'-alpha,4-dimethylbenzylcarbamoyloxy) phenyl-1,1-dimethylurea 3-[3'-alpha isopropyl-4-methoxybenzylcarbamoyloxy) phenyl]-1,1-dimethylurea 3-[3'-alpha-n-propylbenzylcarbamoyloxy)phenyl]-1,1-dimethylurea 3-[3'-(N'-diphenylmethylcarbamoyloxy)phenyl]-1,1-dimethylurea 3-(3-chlorophenoxy)ethylcarbamoyloxy)phenyl]-1,1-dimethylurea 3-[3'-(N'-2-(1-naphthoxy)ethylcarbamoyloxy)-phenyl]-1,1-dimethylurea 3-[3'-(N'-2-(2-naphthoxy)ethylcarbamoyloxyphenyl]-1,1-dimethylurea 3-[3'-(N'-2-(4-chlorophenoxy)ethylcarbamoyloxy)-phenyl]-1,1-dimethylurea 3-[3'-(N'-methyl-N'-2-(3-chlorophenoxy)ethylcarbamoyloxy)phenyl[-1,1-dimethylurea 3-[3'-(N'-benzylthiocarbamoylthiol)phenyl]-1,1-dimethylurea 3-[3'-(N'-allyl-N'-2,6-dichlorobenzylcarbamoyloxy)phenyl]-1,1-dimethylurea 3-[3'-(N'-isopropyl-N'-2,6-dichlorobenzylcarbamoyloxy)phenyl]-1,1-dimethylurea 3-[3'-(N'-isopropyl-N'-2-chlorobenzylcarbamoyloxy)phenyl]-1,1-dimethylurea.

3-[3'-(N'-allyl-N'-2-chlorobenzylcarbamoyloxy)phenyl]-1,1-dimethylurea

3-[3'-N'-allyl-N'-4-chlorobenzylcarbamoyloxy)phenyl]-1,1-dimethylurea

3-[3'-(N'-allyl-N'-2,4-dichlorobenzylcarbamoyloxy)phenyl]-1,1-dimethylurea

3-[3'-(N'-allyl-N'-2,6-dichlorobenzylcarbamoyloxy)phenyl]-1,1-dimethylurea

3-[3'-(N'-allyl-N'-alpha-methylphenethylcarbamoyloxy)phenyl]-1,1-dimethylurea

3-[3'-(N'-allyl-N'-phenethylcarbamoyloxy)phenyl]-1,1-dimethylurea

3-[3'-(N'-allyl-N'-benzylcarbamoyloxy)phenyl]-1,1-dimethylurea

3-[3'-(N'-butyl-N'-2-chlorobenzylcarbamoyloxy)phenyl]-1,1-dimethylurea

3-[3'-(N'-tert.butyl-N'-2-chlorobenzylcarbamoyloxy)phenyl]-1,1-dimethylurea

3-[3'-(N'-tert.butyl-N'-4-chlorobenzylcarbamoyloxy)phenyl]-1,1-dimethylurea

3-[3'-(N'-sec.butyl-N'-4-chlorobenzylcarbamoyloxy)phenyl]-1,1-dimethylurea

3-[3'-(N'-tert.butyl-N'-2,4-dichlorobenzylcarbamoyloxy)phenyl]-1,1-dimethylurea

3-[3'-(N'-cyclohexyl-N'-4-clorobenzylcarbamoyloxy)phenyl]-1,1-dimethylurea

3-[3'-(N'-2-chloroallyl-N'-benzylcarbamoyloxy)phenyl]-1,1-dimethylurea

3-[3'-(N'-methyl-N'-2-(4-chloro-2-methylphenoxy)ethylcarbamoyloxy)phenyl]-1,1-dimethylurea 3-[3'-(N'-methyl-N'-2-(2-chlorophenoxy)ethylcarbamoyloxy)phenyl]-1,1-dimethylurea 3-[3'-(N'-methyl-N'-2-(3-chlorophenoxy)ethylcarbamoyloxy)phenyl 1,1-dimethylurea 3-[3'-(N'-methyl-N'-2-(4-chlorophenoxy)ethylcarbamoyloxy)phenyl]-1,1-dimethylurea 3-[3'-(N'-methyl-N'-2-(2,4-dichlorophenoxy)ethylcarbamoyloxy)phenyl]-1,1-dimethylurea 3-[3'-(N'-methyl-N'-2-(1-naphthoxy)ethylcarbamoyloxy)phenyl]-1,1-dimethylurea 3-[3'-(N'-isopropyl-N'-2-(1-naphthoxy)ethylcarbamoyloxy)phenyl]-1,1-dimethylurea 3-[3'-(N'-methyl-N'-2-(2-naphthoxy)ethylcarbamoyloxy)phenyl]-1,1-dimethylurea 3-[3'-(N'-methyl-N'-4-phenoxybutylcarbamoyloxy)phenyl]-1,1-dimethylurea 3-[3'-(N'-methyl-N'-2-phenoxyethylcarbamoyloxy)phenyl]-1,1-dimethylurea 3-[3'-(N'-methyl-N'-3-phenoxypropylcarbamoyloxy)phenyl]-1,1-dimethylurea 3-[3'-(N'-2,3-dichloroallyl-N'-benzylcarbamoyloxy)phenyl]-1,1-dimethylurea 3-[3'-(N'-methyl-N'-3,4-dichlorobenzylcarbamoyloxy)phenyl]-1,1-dimethylurea 3-[3'-(N'-methyl-N'-alpha-methylbenzylcarbamoyloxy)phenyl]-1,1-dimethylurea 3-[3'-(N'-1,3-dimethylbutyl-N'-4-chlorobenzylcarbamoyloxy)phenyl]-1,1-dimethylurea 3-[3'-(N'-1,3-dimethylbutyl-N'-2,4-dichlorobenzylcarbamoyloxy)phenyl]-1,1-dimethylurea 3-[3'-(N'-methyl-N'-alpha-methyl-4-chlorobenzylcarbamoyloxy)phenyl]-1,1-dimethylurea 3-[3'-(N'-methyl-N'-alpha-methylphenethylcarbamoyloxy)phenyl]-1,1-dimethylurea 3-[3'-(N'-ethyl-N'-1-naphthylmethylcarbamoyloxy)phenyl]-1,1-dimethylurea 3-[3'-(N'-methyl-N'-2-fluorobenzylcarbamoyloxy)phenyl]-1,1-dimethylurea 3-[3'-(N'-methyl-N'-alpha-methylene-2,4,6-trimethylbenzylcarbamoyloxy)phenyl]-1,1-dimethylurea 3-[3'-(N'-2,2,3-trichloroallyl-N'-benzylcarbamoyloxy)phenyl]-1,1-dimethylurea 3-[3'-(N'-4-bromo-alpha-methylbenzylcarbamoyloxy)phenyl]-1,1-dimethylurea 3-[3'-(N'-alpha-tert.butyl-4-methoxybenzylcarbamoyloxy)phenyl]-1,1-dimethylurea 3-[3'-(N'-2-(4-chloro-2-methylphenoxy)ethylcarbamoyloxy)phenyl]-1,1-dimethylurea 3-[3'-(N'-5-(2-chlorophenoxy)pentylcarbamoyloxy)phenyl]-1,1-dimethylurea 3-[3'-(N'-2-(4-chloro-2,5-xylyloxy)ethylcarbamoyloxy)phenyl]-1,1-dimethylurea 3-[3'-(N'-2-(4-chloro-3,5-xylyloxy)ethylcarbamoyloxy)phenyl]-1,1-dimethylurea 3-[3'-(N'-2,2-dimethyl-3-phenylpropylcarbamoyloxy)phenyl]-1,1-dimethylurea 3-[3'-(N'-alpha-methyl-3-methoxybenzylcarbamoyloxy)phenyl]-1,1-dimethylurea 3-[3'-(N'-alpha-methyl-3,4-dichlorobenzylcarbamoyloxy)phenyl]-1,1-dimethylurea 3-[3'-(N'-alpha,2,4-trimethylbenzylcarbamoyloxy)phenyl]-1,1-dimethylurea The following urea-carbanilates were also prepared by substantially the same procedure as previously shown. Sulfur analogs of the carbanilate group will be represented as follows:

$$-\overset{|}{N}-\overset{\overset{O}{\|}}{C}-OR \quad \text{carbanilic acid}$$

$$-\overset{|}{N}-\overset{\overset{O}{\|}}{C}SR \quad \text{thiolcarbanilic acid'}$$

$$-\overset{|}{N}-\overset{\overset{S}{\|}}{C}-OR \quad \text{thionocarbanilic acid}$$

$$-\overset{|}{N}-\overset{\overset{S}{\|}}{C}-SR \quad \text{dithiocarbanilic acid}$$

The nitrogen of the urea group attached to the metabifunctional phenyl ring will be the "3" nitrogen and the other nitrogen the "1" nitrogen.

methyl ester m-[3-(1-ethyl)-2-thioureido]dithiocarbanilic acid ethyl ester m-[3-(1-ethyl)-2-thioureido]carbanilic acid ethyl ester m-[3-(1-phenyl)-2-thioureido]carbanilic acid methyl ester m-[3-(1-ethyl)-2-thioureido]carbanilic acid methyl ester m-[3-(1-t-butyl)-2-thioureido]thiolcarbanilic acid methyl ester m-[3-(1-(4'-phenoxy)phenyl)-2-thioureido]carbanilic acid methyl ester m-[3-(1-3'-methylthio)phenyl)ureido]carbanilic acid phenyl ester m-[3-(1-(3'-methylthio)phenyl)ureido]carbanilic acid iospropyl ester m-[3-(1-(3'-methylthio)phenyl)ureido]carbanilic acid methyl ester m-[3-(1-(3'-trifluoromethyl)phenyl)ureido]carbanilic acid isopropyl ester m-[3-(1-(3'-trifluoromethyl)phenyl)ureido]carbanilic acid phenyl ester m-[3-(1-(3'-trifluoromethyl)phenyl)ureido]carbanilic acid methyl ester m-[3-(1-(3'-methylthio)phenyl)thioureido]carbanilic acid methyl ester m-[3-(1-(3'-trifluoromethyl)phenyl)thioureido]carbanilic acid phenyl ester m-[3-(1-(3'-trifluoromethyl)phenyl)thioureido]carbanilic acid phenyl ester m-[3-(1-(3'-methylthio)phenyl)thioureido]carbanilic acid phenyl ester m-[3'-(1-(3'-fluoro)phenyl)thioureido]carbanilic acid methyl ester m-[3-(1,1-dimethyl)ureido]-thiolcarbanilic acid isopropyl ester m-[3-(1-allyl)thioureido]carbanilic acid isopropyl ester m-[3-(1-phenyl)thioureido]carbanilic acid ethyl ester m-[3-(1,1-dimethyl)ureido]thiolcarbanilic acid ethyl ester m-[3-(1,1-piperidyl)ureido]thiolcarbanilic acid methyl ester m-[3-(1-t-butyl)thioureido]carbanilic acid methyl ester m-[3-(1,1-piperidyl)thioureido]carbanilic acid methyl ester m-[3-(1,1-di-isopropyl)thioureido]carbanilic acid methyl ester m-[3-(1,1-diethyl)thioureido]carbanilic acid methyl ester m-[3-(1,1-diallyl)thioureido]carbanilic acid isopropyl ester m-[3-(1-t-butyl)thioureido]carbanilic acid methyl ester m-[3-(1-t-butyl)ureido]carbanilic acid methyl ester m-[3-(1-methyl)ureido]carbanilic acid The following di-urea compounds were prepared by substantially the same procedure as previously shown.

1-methyl-3-[3'-(1-(3'',4''-dichloro)phenyl)ureido]-phenylthiourea 1-ethyl-3-[3'-(1-(3'', 4''-dichloro)phenyl)thioureido]phenylthiourea 1,1-dimethyl-3-[3'-(1-(2-chloroallyl)thioureido]-phenylurea 1,1-dimethyl-3-[3'-(1-(3'',4''-dichloro)phenyl)thiourea]phenylurea 1,1-dimethyl-3-[3'-(1-allyl)thioureido]phenylurea 1-t-butyl-3-[3'-(1,1-dimethyl)ureido]phenylthiourea 1-(2-chloroallyl)-1-methyl-3-[3'-(1,1-dimethyl)ureido]phenylthiourea 1,1-dimethyl-3-[3'-(1-(2-phenoxy)ethyl)ureido]-phenylurea 1,1-dimethyl-3-[3'-(1-(2-o-chlorophenoxy)ethyl]ureido]phenylurea In accordance with this invention it has been found that the growth of dormant seeds, germinant seeds, germinative seeds, emerging seedlings and established woody and herbaceous vegatation can be modified by exposing the seeds, emerging seedlings, of the roots or aboveground portions of established vegetation, to the action of an effective amount of the compounds of the present invention. The compounds can be used as individual compounds, as admixtures of two or more compounds, or in admixture with an adjuvant. These compounds are effective as postemergent herbicides and pre-emergant herbicides, but their most outstanding utility is as selective pre-emergant and postemergent activity, e.g. the selective control of the growth of one or more monocotyledonous species and/or one or more dicotyledonous species in the presence of other monocotyledons and/or dicotyledons. Furthermore, these compounds are characterized by broad spectrum activity; i.e. they modify the growth of a wide variety of plants.

For the sake of brevity and simplicity, the term "active ingredient" will be used hereinafter to describe the present 3'-(carbamoyloxy)ureas; ureidoureas and ureacarbanilates.

The herbicidal compositions of this invention contain at least one active ingredient and an adjuvant in liquid or solid form. The composition are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvent such as a finely-divided solid, a liquid of organic origin, water, a wetting agent, a dispersing agent, an emulsifying agent or any suitable combination of these.

The term "herbicidal composition" as used herein and in the appended claims is intended to mean not only compositions in a suitable form for application but also concentrated compositions which require dilution or extension with a suitable quantity of liquid or solid adjuvant prior to application.

The pre-emergent herbicidal activity of illustrative compounds of this invention is demonstrated as follows:

A good grade of top soil is placed in aluminum pans and compacted to a depth of three eighths to inch half inches from the top of each pan. A predetermined number of seeds of each of various plant species are placed on top of the soil in each pan. The herbicidal compositions are applied to the soil by admixture with or incorporation in the top soil layer.

In the surface application method the seeds are covered with a three eighths inch layer of prepared soil and the pan leveled. The herbicidal composition is applied by spraying the surface of the top layer of soil, prior to watering the seeds, with a solution containing a sifficient amount of active ingredient to obtain the desired rate per acre on the soil surface.

In the soil incorporation method, the soil required to cover the seeds is weighed and admixed with a herbicidal composition containing a known amount of active ingredient. The pans are then filled with the admixture and leveled. Watering is carried out by permitting the soil in the pans to absorb moisture through the apertured bottom of the pans. The seed containing pans are placed on a sand bench and maintained for approximately 14 or 28 days under ordinary conditions of sunlight and watering. The plants are observed at the end of approximately 14 or 28 days and the results recorded.

The pre-emergent herbicidal activity of the active ingredients is measured by the average percent control of each seed lot. The average percent control is converted to a relative numerical scale for the sake of brevity and simplicity in the examples. The pre-emergent herbicidal activity index used in the Tables is defined as follows:

| Average Percent Control | | Numerical Scale |
|---|---|---|
| 0 – 25 | = | 0 |
| 26 – 50 | = | 1 |
| 51 – 75 | = | 2 |
| 76 – 100 | = | 3 |

The pre-emergent herbicidal activity of some of the 3′-(carbamoyloxy)ureas of this invention is recorded in Table I for various application rates of the active ingredients. The data recorded in Table I is observation after 14 days unless otherwise indicated.

organic solvent-water solution containing the active ingredient, is applied to the plants in different set of pans at defined rates per acre. The treated plants are placed in a greenhouse and the effects observed and recorded after approximately 14 days or approximately 28 days. The data recorded in Tables II, III and IV is for 14 day observations on 21 day old specimen unless otherwise indicated.

The post-emergent herbicidal activity index used in Tables II, III and IV is measured by the average percent control of each plant species and is defined as follows:

TABLE I

PRE-EMERGENT HERBICIDAL ACTIVITY

| Compound | Rate lb/acre | Sugar Beet | Cotton | Soybean | Corn | Wheat | Rice | Pigweed | Smartweed | Cocklebur | Lambsquarter | Hemp Sesbania |
|---|---|---|---|---|---|---|---|---|---|---|---|---|
| I | 1 | 2 | 0 | 0 | 0 | 0 | 1 | 3 | 0 | 0 | 1 | 3 |
| II | 1 | — | — | — | — | — | — | — | 3 | 2 | 1 | — |
| III | 1 | 3 | — | 0 | — | 0 | 0 | — | 3 | 0 | 3 | 2 |
| IV | 5 | — | — | — | — | — | — | — | 2 | 1 | 3 | — |
| V | 1 | 3 | — | 1 | — | 0 | 0 | — | 3 | 1 | 2 | 3 |
| VI | 2 | 2 | 0 | 0 | 1 | 0 | 1 | 1 | 1 | 1 | 1 | 1 |
| VII | 1 | 1 | 2 | 0 | 0 | 0 | 0 | 3 | 2 | 0 | 3 | 1 |
| VIII | 2 | 3 | 2 | 0 | 0 | 0 | 0 | 3 | 0 | 0 | 3 | 1 |

| Compound | Rate lb/acre | Velvet Leaf | Wild Oat | Brome Grass | Barnyard Grass | Crab Grass | Canada Thistle | Morning Glory | Yellow Nutsedge | Quack Grass | Johnson Grass | Wild Buckwheat | Panicum |
|---|---|---|---|---|---|---|---|---|---|---|---|---|---|
| I | 1 | 2 | 0 | 0 | 0 | 0 | — | — | — | — | — | — | — |
| II | 1 | 3 | — | 0 | 2 | — | 0 | 1 | 1 | 2 | 0 | — | — |
| III | 1 | 3 | — | 0 | 1 | 3 | — | 0 | — | — | — | 1 | 0 |
| IV | 5 | 1 | — | 1 | 0 | — | 1 | 2 | 0 | 0 | 1 | — | — |
| V | 1 | 3 | — | 0 | 2 | 2 | — | 3 | — | — | — | 1 | 0 |
| VI | 2 | 0 | 1 | 0 | 1 | 2 | — | — | — | — | — | — | — |
| VII | 1 | 0 | 0 | 0 | 0 | 0 | — | — | — | — | — | — | — |
| VIII | 2 | 2 | 1 | 0 | 1 | 2 | — | — | — | — | — | — | — |

| Compound | | |
|---|---|---|
| | I | 3-[3′-(N′-alpha methylbenzylcarbamoyloxy)phenyl]-1,1-dimethylurea |
| | II | 3-[3′-(N′-alpha-n-propylbenzylcarbamoyloxy)phenyl]-1,1-dimethylurea |
| | III | 3-[3′-(N′-(1,1-dimethyl-2-phenylethylcarbamoyloxy)phenyl]-1,1-dimethylurea |
| | IV | 3-[3′-(N′-methylcarbamoyloxy)phenyl]-1-allylthiourea |
| | V | 3-[3′-(N′-alpha methyl-4-chlorobenzylcarbamoyloxy)phenyl]-1,1-dimethylurea |
| | VI | ethyl N-[3-(1,1-dimethyl)ureido]thiolcarbanilate |
| | VII | phenyl N-[3-(1-m-trifluoromethyl)ureido]carbanilate |
| | VIII | 1-t-butyl-3-[3′-(1,1-dimethyl)ureido]phenylthiourea |

Although the compounds of this invention possess pre-emergent activity, they are more active as post-emergent herbicides. This is illustrated by the following:

The active ingredients are applied in spray form to 14-day or 21 day old plants species. The spray, an

| Average Percent Control | Numerical Scale |
|---|---|
| 0 – 25 | 0 |
| 26 – 50 | 1 |
| 51 – 75 | 2 |
| 76 – 99 | 3 |
| 100 | 4 |

TABLE II

POST-EMERGENT HERBICIDAL DATA-CARBAMOYLOXY-UREAS

| Compounds | % Conc | Canada Thistle | Cocklebur | Velvet Leaf | Morning Glory | Lambsquarter | Smartweed | Yellow Nutsedge | Quack Grass | Johnson Grass | Brome Grass | Barnyard Grass |
|---|---|---|---|---|---|---|---|---|---|---|---|---|
| I | 0.2 | 2 | 4 | 4 | 4 | 4 | 4 | 0 | 4 | 0 | 2 | 2 |
| II | 0.2 | 0 | 3 | 2 | 3 | 4 | 4 | 0 | 1 | 1 | 1 | 2 |
| III | 0.2 | 1 | 3 | 1 | 2 | 3 | 2 | 0 | 1 | 0 | 1 | 2 |
| IV | 0.2 (a) | 4 | 4 | 4 | 4 | 4 | — | 0 | 1 | — | 1 | 2 |
| V | 0.2 (a) | — | 4 | 3 | 4 | 4 | 4 | 1 | 2 | 0 | 1 | 2 |

(a) active ingredient applied to 14 day old plant specimen
Compound I  – 1,1-dimethyl-3-[3′-(N′-methyl-N′-2-m-chlorophenoxyethylcarbamoyloxy)phenyl]urea
Compound II  1 -1,1-dimethyl-3-[3′-(N′-1,1-dimethyl-2-phenylcarbamoyloxy)phenyl]urea
Compound III  – 1,1-dimethyl-3-[3-(N′-methyl-N′-2-(2-methyl-4-chlorophenyl)ethylcarbamoyloxy)phenyl]urea
Compound IV  – 1,1-dimethyl-3-[3′-(N′-4-methylbenzylcarbamoyloxy)phenyl]urea
Compound V  – 1,1-dimethyl-3-[3′-(N′-alpha isopropylbenzylcarbamoyloxy)phenyl]urea

TABLE III

POST-EMERGENT HERBICIDAL ACTIVITY-UREA-CARBANILATES

| Compound | % Conc | Sugar Beet | Cotton | Soybean | Corn | Wheat | Rice | Pigweed | Smartweed | Cocklebur | Lambsquarter | Hemp Sesbania | Velvet Leaf | Wild Oat | Brome Grass | Barnyard Grass | Crab Grass |
|---|---|---|---|---|---|---|---|---|---|---|---|---|---|---|---|---|---|
| I   | 0.2 | 3 | 2 | 3 | 0 | 0 | 3 | 3 | 4 | 3 | 4 | 4 | 0 | 1 | 1 | 1 | 3 |
| II  | 0.2 | 3 | 0 | 1 | 1 | 0 | 0 | 4 | 4 | 0 | 4 | 4 | 2 | 1 | 1 | 2 | 3 |
| III | 0.2 | 4 | 1 | 3 | 1 | 0 | 0 | 4 | 4 | 1 | 3 | 4 | 2 | 1 | 2 | 3 | 2 |

Compound I - methyl N-[3-(1-t-butylureido)phenyl]thiolcarbanilate
Compound II - methyl N-[3-(1-(4-phenoxy)phenylthioureido)phenyl]carbanilate
Compound III - methyl N-[3-(1-t-butylthioureido)phenyl]carbanilate

TABLE IV

POST-EMERGENT HERBICIDAL ACTIVITY-DI-UREAS

| Compound | % Conc | Sugar Beet | Cotton | Soybean | Corn | Wheat | Rice | Pigweed | Smartweed | Cocklebur | Lambsquarter | Hemp Sesbania | Velvet Leaf | Wild Oats | Brome Grass | Barnyard Grass | Crab Grass |
|---|---|---|---|---|---|---|---|---|---|---|---|---|---|---|---|---|---|
| I   | 0.05     | 4 | 1 | 3 | 1 | 1 | 1 | 4 | 4 | 3 | 4 | 3 | 2 | 2 | 2 | 2 | 3 |
| II  | 0.05 (a) | 3 | 1 | 1 | 1 | 2 | 3 | 4 | 2 | 1 | 3 | 3 | 1 | 1 | 2 | 2 | 2 |
| III | 0.05     | 4 | 2 |   | 1 | 1 | 2 | 4 | 4 | 4 | 4 | 4 | 2 | 1 | 1 | 2 | 3 |
| IV  | 0.01     | 4 | 2 | 1 | 0 | 0 | 0 | 4 | 3 | 0 | 4 | 4 | 1 | 0 | 1 | 0 | 1 |

Compound I - 1,1-dimethyl-3-[3'-(1-(2-chloroallyl)thioureido)phenyl]urea
Compound II - 1,1-dimethyl-3-[3'-(1-(3,4-dichlorophenyl)thioureido)phenyl]urea
Compound III - 1-t-butyl-3-[3'-(1,1-dimethylureido)phenyl]urea
Compound IV - 1-methyl-1-(2-chloroallyl)-3-[3'-(1,1-dimethylureido)phenyl]thiourea In addition to the general herbicidal activity of the compounds of this invention, they also exhibit selective activity on weeds in the presence of crops.

As mentioned hereinbefore the herbicidal compositions of this invention comprise an active ingredient and one or more adjuvants which can be solid or liquid extenders, carriers, diluents, conditioning agents and the like. Preferred herbicidal compositions containing the active ingredients of this invention have been developed so that the active ingredients can be used to the greatest advantage to modify the growth of plants. The preferred compositions comprise wettable powders, aqueous suspensions, dust formulations, granules, emulsifiable oils and solutions in solvents. In general, these preferred compositions can all contain one or more surface-active agents.

Surface-active agents which can be used in the phytotoxic compositions of this invention are set out, for example, in Searle U.S. Pat. No. 2,426,417, Todd U.S. Pat. No. 2,655,447, Jones U.S. Pat. No. 2,412,510 and Lenher U.S. Pat. No. 2,139,276. A detailed list of such agents is also set forth by J. W. McCutcheon in "Soap and Chemical Specialties", November 1947, page 8011 et seq., entitled "Synthetic Detergents"; "Detergents and Emulsifiers - Up to Date" (1960), by J. W. McCutcheon, Inc., and Bulletin E-607 of the Bureau of Entomology and Plant Quarantine of the U.S.D.A. In general, less than 50 parts by weight of the surface active agent is present per 100 parts by weight of the herbicidal composition.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylinic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

The wettable powders compositions of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required from about 0.1 to 2.0 parts by weight of the solid inert extender can be replaced by a corrosion inhibitor or antifoaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed coverage is very uniform.

Dusts are dense finely-divided particulate compositions which are intended for application to the soil in dry form. Dusts are characterized by their free-flowing and rapid settling properties so that they are not readily wind-borne to areas where they are of no value. Dusts contain primarily an active ingredient and a dense, free-flowing finely-divided particulate extender. However, their performance is sometimes aided by the inclusion of a wetting agent such as those listed hereinbefore under wettable powder compositions and convenience in manufacture frequently demands the inclusion of an inert, absorptive grinding aid. Suitable classes of grinding aids are natural clays, diatomaceous earth and synthetic minerals derived from silica or silicate. Preferred grinding aids include attapulgite clay, diatomaceous silica, synthetic fine silica and synthetic calcium and magnesium silicates.

The inert finely-divided solid extender for the dusts can be either of vegetable or mineral origin. The solid extenders are characterized by possessing relatively low surface areas and are poor in liquid absorption. Suitable inert solid extenders for plant growth regulant dusts include micaceous talcs, pyrophyllite, dense kaolin clays, ground calcium phosphate rock and tobacco dust. The dusts usually contain from about 0.5 to 95 parts active ingredient, 0 to 50 parts grinding aid, 0 to 50 parts wetting agent and 5 to 99.5 parts dense solid extender, all parts being by weight and based on the total weight of the dust.

The wettable powders described above may also be used in the preparation of dusts. While such wettable powders could be used directly in dust form, it is more advantageous to dilute them by blending with the dense dust diluent. In this manner, dispersing agents, corrosion inhibitors, and anti-foam agents may also be bound as components of a dust.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. Suitable surface active agents are anionic, cationic and non-ionic such as alkyl aryl polyethoxy alcohols, polyethylene sorbitol or sorbitan fatty acid esters, polyethylene glycol fatty esters, fatty alkyllol amide condensates, amide salts of fatty alcohol sulfates together with long chain alcohols and oil soluble petroleum sulfonates or mixtures thereof. The emulsifiable oil compositions generally contain from about 5 to 95 parts active ingredient, about 1 to 50 parts surface active agent and about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore under wettable powders can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the herbicidal granules.

The mineral particles which are used in the granular herbicidal compositions of this invention usually have a size range of 10 to 100 mesh, but preferably such that a large majority of the particles have from 14 to 16 mesh with the optimum size being from 20 to 40 mesh. Clay having substantially all particles between 14 and 80 mesh and at least about 80 percent between 20 and 40 mesh is particularly preferred for use in the present granular composition. The term "mesh" as used herein means U.S. Sieve Series.

The granular herbicidal compositions of this invention generally contain from about 5 parts to about 30 parts by weight of active ingredient per 100 parts by weight of clay and 0 to about 5 parts by weight of surface active agent per 100 parts by weight of particulate clay. The preferred herbicidal granular compositions contain from about 10 parts to about 25 parts by weight of active ingredient per 100 parts by weight of clay.

The herbicidal compositions of this invention can also contain other additaments, for example fertilizers, phtotoxicants, other plant growth regulants, pesticides and the like used as adjuvant or in combination with any of the above-described adjuvants. Chemicals useful in combinations with the active ingredients of this invention include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro,N,N-diallylacetamide
2-chloroallyl diethyldithiocarbamate
N'-(4-chlorophenoxy) phenyl-N,N-dimethylurea
isopropyl M-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
6,7-dihydrodipyrido(1,2-a:2',1'-c)-pyrazidiinium salt
3-(3,4-dichlorophenyl)-1,1-dimethylurea  4,6-dinitro-o-sec-butylphenol
2-methyl-4,6-dinitrophenol
ethyl N,N-dipropylthiolcarbamate
2,3,6-trichlorophenylacetic acid
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha,alpha,alpha-trifluoro-2,6-dinitro-N,N-dipropylp-toluidine
S-propyl dipropylthiolcarbamate
2,4-dichlorophenoxyacetic acid
2',6'-diethyl-N-methoxymethyl-2-chloroacetanilide Fertilizers useful in combination with the active ingredients include for example ammonium nitrate, urea, potash, and superphosphate. Other useful additaments include materials in which plant organisms take root and grow such as compost, manure, humus, sand and the like.

When operating in accordance with the present invention, effective amounts of the active ingredient are dispersed in or on soil or plant growth media and/or applied to aboveground portions of plants, in any convenient fashion. Application to the soil or growth media can be carried out by simply admixing with the soil, by applying to the surface of the soil and thereafter dragging or discing into the soil to the desired depth, or be employing a liquid carrier to accomplish the penetration and impregnation. The application of liquid and particulate solid herbicidal compositions to the surface of soil or to above-ground portions of plants can be carried out by conventional methods, e.g. power dusters, boom and hand sprayers and spray dusters. The compositions can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the herbicide.

The application of an effective amount of the compounds of this invention to the soil or growth media and/or plant is essential and critical for the practice of one embodiment of the present invention. The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment for the modification of vegetative growth, the active ingredients are applied in amounts from about 0.001 to about 25 or more pounds per acre. In applications to soil for the modification of the growth of germinant seeds, germinative seeds, emerging seedlings and established vegetation, the active ingredients are applied in amounts from about 0.1 to about 50 or more pounds per acre. In such soil applications, it is desirable that the active ingredients be distributed to a depth of at least 0.2 inches. In selective pre-emergence herbicidal applications the active ingredients are usually applied in amounts from about 0.1 to 5 pounds per acre. It is believed that one skilled in the art can readily determine from the teachings of this specification, including examples, the approximate application rate for any situation.

The terms "soil" and "growth media" are employed in the present specification and claims in their broadest sense to be inclusive of all conventional "soils" as defined in Webster's New International Dictionary, Second Edition, Unabridged (1961). Thus, the terms refer to any substance or media in which vegetation may take root and grow, and are intended to include not only earth but also compost, manure, muck, humus, sand and the like, adapted to support plant growth.

Although the invention is described with respect to specific modifications, the details thereof are not to be construed as limitations except to the extent indicated in the following claims.

We claim:

1. A meta-bifunctional substituted benzene having the formula

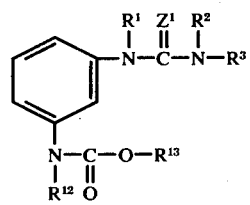

wherein $Z^1$ is selected from the group consisting of oxygen and sulfur; $R^1$ is selected from the group consisting of hydrogen, alkyl having a maximum of 8 carbon atoms and alkenyl having a maximum of 6 carbon atoms; $R^2$ is selected from the group consisting of hydrocarbyl selected from the group consisting of alkyl, alkenyl, alkynyl, and cycloalkyl said alkyl, alkenyl and alkynyl having a maximum of 12 carbon atoms and said cycloalkyl having 3 to 7 ring carbon atoms and a maximum of 4 chain carbon atoms, alkoxy having a maximum of 6 carbon atoms, chloroalkyl having a maximum of 6 carbon atoms and a maximum of 3 halogen atoms, chloroalkenyl having a maximum of 6 carbon atoms and a maximum of 3 halogen atoms, cycloalkenyl having 5 to 7 ring carbon atoms and a maximum of 4 chain carbon atoms, phenyl, substituted phenyl having a maximum of two substituents said substituents being selected from the group consistisng of halogen, nitro and alkyl having a maximum of 4 carbon atoms, the group

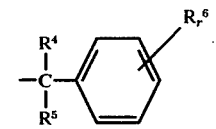

wherein $R^4$ and $R^5$ are each independently selected from the group consisting of hydrogen, alkyl having a maximum of 12 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, $R^6$ is selected from the group consisting of halogen, alkyl having a maximum of 14 carbon atoms, chloroalkyl having a maximum of 3 carbon atoms and a maximum of 3 halogen atoms, nitro, and alkoxy having a maximum of 3 carbon atoms; and $r$ is one of the integers zero-to-three, the group

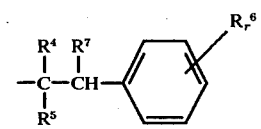

wherein $R^7$ is selected from the group consisting of alkyl and alkenyl each having a maximum of 4 carbon atoms, and $R^4$, $R^5$, $R^6$ and r are as previously defined; and $R^3$ is selected from the group consisting of hydrogen, alkyl having a maximum of 12 carbon atoms, and alkenyl having a maximum of 8 carbon atoms; $R^{12}$ is selected from the group consisting of hydrogen, alkyl having a maximum of 6 carbon atoms and alkenyl having a maximum of 6 carbon atoms; and $R^{13}$ is selected from the group consisting of alkyl having a maximum of 8 carbon atoms, alkenyl having a maximum of 6 carbon atoms, cycloalkyl having from 3 to 7 ring carbon atoms, cyclohexenyl, phenyl, substituted phenyl having a maximum of two substituents said substituents being selected from the group consisting of halogen, nitro and alkyl having a maximum of 4 carbon atoms, the group

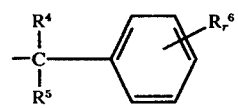

and the group

-continued

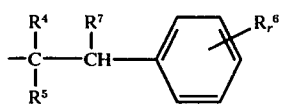

wherein $R^4$, $R^5$, $R^6$, $R^7$ and r are as previously defined.

2. A meta-bifunctional substituted benzene according to claim 1 in which only one of $R^4$ and $R^5$ is alkenyl or chloroalkenyl and $R^7$ is other than alkenyl when either $R^4$ or $R^5$ is alkenyl or chloroalkenyl.

3. A meta-bifunctional substituted benzene according to claim 2 in which $R^1$ and $R^{12}$ are each independently selected from the group consisting of hydrogen and alkyl having a maximum of 4 carbon atoms.

4. A meta-bifunctional substituted benzene according to claim 3 in which $R^1$ and $R^{12}$ are both hydrogen.

5. A herbicidal method which comprises applying to plants a herbicidal effective amount of a metal-bifunctional substituted benzene of the formula

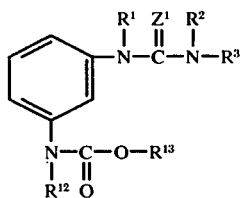

wherein $Z^1$ is selected from the group consisting of oxygen and sulfur; $R^1$ is selected from the group consisting of hydrogen, alkyl having a maximum of 8 carbon atoms and alkenyl having a maximum of 6 carbon atoms; $R^2$ is selected from the group consisting of hydrocarbyl selected from the group consisting of alkyl, alkenyl, alkynyl and cycloalkyl said alkyl, alkenyl and alkynyl having a maximum of 12 carbon atoms and said cycloalkyl having 3 to 7 ring carbon atoms and a maximum of 4 chain carbon atoms, alkoxy having a maximum of 6 carbon atoms, chloroalkyl having a maximum of 6 carbon atoms and a maximum of 3 halogen atoms, chloroalkenyl having a maximum of 6 carbon atoms and a maximum of 3 halogen atoms, cycloalkenyl having 5 to 7 ring carbon atoms and a maximum of 4 chain carbon atoms, phenyl, substituted phenyl having a maximum of two substituents said substituents being selected from the group consisting of halogen, nitro and alkyl having a maximum of 4 carbon atoms, the group

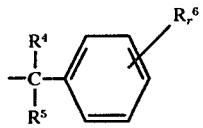

wherein $R^4$ and $R^5$ are each independently selected from the group consisting of hydrogen, alkyl having a maximum of 12 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, $R^6$ is selected from the group consisting of halogen, alkyl having a maximum of 14 carbon atoms, chloroalkyl having a maximum of 3 carbon atoms and a maximum of 3 halogen atoms, nitro, and alkoxy having a maximum of 3 carbon atoms; and r is one of the integers zero to three; the group

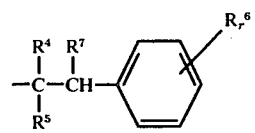

wherein $R^7$ is selected from the group consisting of alkyl and alkenyl each having a maximum of 4 carbon atoms, and $R^4$, $R^5$, $R^6$ and r are as previously defined; and $R^3$ is selected from the group consisting of hydrogen, alkyl having a maximum of 12 carbon atoms, and alkenyl having a maximum of 8 carbon atoms; $R^{12}$ is selected from the group consisting of hydrogen, alkyl having a maximum of 6 carbon atoms and alkenyl having a maximum of 6 carbon atoms; and $R^{13}$ is selected from the group consisting of alkyl having a maximum of 8 carbon atoms, alkenyl having a maximum of 6 carbon atoms, cycloalkyl having from 3 to 7 ring carbon atoms, cyclohexenyl, phenyl, substituted phenyl having a maximum of two substituents said substituents being selected from the group consisting of halogen, nitro and alkyl having a maximum of 4 carbon atoms, the group

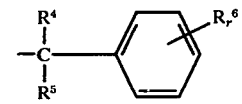

and the group

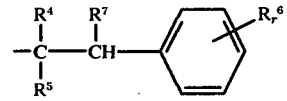

wherein $R^4$, $R^5$, $R^6$, $R^7$ and r are as previously defined.

6. A herbicidal composition comprising an adjuvant and a herbicidal effective amount of a meta-bifunctional substituted benzene of the formula

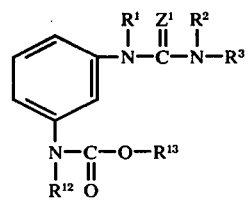

wherein $Z^1$ is selected from the group consisting of oxygen and sulfur; $R^1$ is selected from the group consisting of hydrogen, alkyl having a maximum of 8 carbon atoms and alkenyl having a maximum of 6 carbon atoms; $R^2$ is selected from the group consisting of hydrocarbyl selected from the group consisting of alkyl, alkenyl, alkynyl and cycloalkyl said alkyl, alkenyl and alkynyl having a maximum of 12 carbon atoms and said cycloalkyl having 3 to 7 ring carbon atoms and a maximum of 4 chain carbon atoms, alkoxy having a maximum of 6 carbon atoms, chloroalkyl having a maximum of 6 carbon atoms and a maximum of 3 halogen atoms, chloroalkenyl having a maximum of 6 carbon atoms and a maximum of 3 halogen atoms, cycloalkenyl having 5 to 7 ring carbon atoms and a maximum of 4 chain carbon atoms, phenyl, substituted phenyl having a maximum of two substituents said substituents being selected from the group consisting of halogen, nitro and alkyl having a maximum of 4 carbon atoms, the group

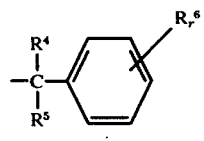

wherein $R^4$ and $R^5$ are each independently selected from the group consisting of hydrogen, alkyl having a maximum of 12 carbon atoms, alkenyl having a maximum of 3 carbon atoms, chloroalkyl having a maximum of 3 carbon atoms and a maximum of 3 halogen atoms, chloroalkenyl having a maximum of 3 carbon atoms and 3 halogen atoms, $R^6$ is selected from the group consisting of halogen, alkyl having a maximum of 14 carbon atoms, chloroalkyl having a maximum of 3 carbon atoms and a maximum of 3 halogen atoms, nitro, and alkoxy having a maximum of 3 carbon atoms; and r is one of the integers zero to three, the group

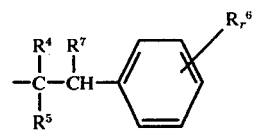

wherein $R^7$ is selected from the group consisting of alkyl and alkenyl each having a maximum of 4 carbon atoms, and $R^4$, $R^5$, $R^6$ and r are as previously defined; and $R^3$ is selected from the group consisting of hydrogen, alkyl having a maximum of 12 carbon atoms, and alkenyl having a maximum of 8 carbon atoms; $R^{12}$ is selected from the group consisting of hydrogen, alkyl having a maximum of 6 carbon atoms and alkenyl having a maximum of 6 carbon atoms; and $R^{13}$ is selected from the group consisting of alkyl having a maximum of 8 carbon atoms, alkenyl having a maximum of 6 carbon atoms, cycloalkyl having from 3 to 7 ring carbon atoms, cyclohexenyl, phenyl, substituted phenyl having a maximum of two substituents said substituents being selected from the group consisting of halogen, nitro and alkyl having a maximum of 4 carbon atoms, the group

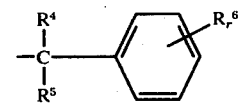

and the group

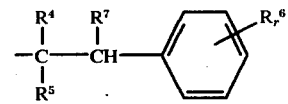

wherein $R^4$, $R^5$, $R^6$, $R^7$ and r are as previously defined.

* * * * *